United States Patent [19]

Sanese

[11] Patent Number: 5,722,949
[45] Date of Patent: Mar. 3, 1998

[54] FLUID SUPPLY AND SUCTION APPARATUS AND METHOD

[75] Inventor: Christopher N. Sanese, Columbus, Ohio

[73] Assignee: Sanese Medical Corporation, Columbus, Ohio

[21] Appl. No.: 572,122

[22] Filed: Dec. 14, 1995

Related U.S. Application Data

[63] Continuation-in-part of Ser. No. 296,950, Aug. 26, 1994, abandoned.

[51] Int. Cl.⁶ .................................................. A61M 1/00
[52] U.S. Cl. .......................... 604/33; 604/28; 604/35; 604/119; 604/249
[58] Field of Search ........................... 604/27, 30, 33, 604/35, 36, 38, 240, 247, 248, 249, 256, 118, 119, 28, 246, 902; 600/131; 137/625.41, 625.47

[56] References Cited

U.S. PATENT DOCUMENTS

| | | |
|---|---|---|
| 3,965,910 | 6/1976 | Fischer . |
| 4,504,266 | 3/1985 | Härle . |
| 4,526,573 | 7/1985 | Lester et al. . |
| 4,705,073 | 11/1987 | Beck . |
| 4,881,523 | 11/1989 | Heckele ................... 128/4 |
| 4,957,483 | 9/1990 | Gonser et al. . |
| 5,034,000 | 7/1991 | Freitas et al. . |
| 5,178,606 | 1/1993 | Ognier et al. . |
| 5,186,714 | 2/1993 | Boudreault et al. . |
| 5,188,591 | 2/1993 | Dorsey, III . |
| 5,197,948 | 3/1993 | Ghodsian . |
| 5,205,816 | 4/1993 | Dodson et al. . |
| 5,224,929 | 7/1993 | Remiszewski . |
| 5,241,990 | 9/1993 | Cook . |
| 5,242,387 | 9/1993 | Loughlin . |
| 5,244,459 | 9/1993 | Hill . |
| 5,254,083 | 10/1993 | Gentelia et al. . |
| 5,295,956 | 3/1994 | Bales et al. ................ 604/30 |
| 5,314,406 | 5/1994 | Aries et al. . |
| 5,322,503 | 6/1994 | Desai . |
| 5,348,555 | 9/1994 | Zinnanti . |
| 5,354,291 | 10/1994 | Bales et al. ................ 604/35 |
| 5,391,145 | 2/1995 | Dorsey, III . |
| 5,449,357 | 9/1995 | Zinnanti ................... 606/49 |
| 5,514,089 | 5/1996 | Walbrink et al. ......... 604/33 |
| 5,562,640 | 10/1996 | McCabe et al. .......... 604/280 |

*Primary Examiner*—Corrine M. McDermott
*Assistant Examiner*—Deborah B. Blyveis
*Attorney, Agent, or Firm*—Dinsmore & Shohl LLP

[57] ABSTRACT

An improved fluid supply and suction apparatus and method for supplying and suctioning fluid through a cannula into and through the body of the fluid supply and suction apparatus is shown. The fluid supply and suction apparatus, which is intended for use in a surgical enviornment, preferably comprises a body having a plurality of ports in fluid communication with a tool insertion thru-hole. The tool insertion thru-hole provides a substantially unobstructed portal from one end of the apparatus body to the other end of the apparatus body. In a more preferred embodiment, the plurality of ports are open to one end of the apparatus body only and they comprise at least a fluid supply port, a fluid suction port, and a regulated port having a suction regular to selectively control the amount of suction through the regulated port. Valves are preferably provided to control flow to and from the ports into and out of the tool insertion thru-hole. In normal operation, fluid supply and suction tubes are connected to each port providing either fluid supply or suction as appropriate. At one end of the apparatus body, a cannula is attached which transports fluid to the surgical site or transports fluid being suctioned from the surgical site. The subject apparatus can be used with fluids comprising gases, liquids or liquids which contained entrained solid matter or mixtures thereof.

14 Claims, 4 Drawing Sheets

FLUID SUPPLY AND SUCTION APPARATUS AND METHOD

RELATED APPLICATIONS

This application is a continuation-in-part of application Ser. No. 08/296,950 filed Aug. 26, 1994, now abandonded.

FIELD OF THE INVENTION

The present invention relates generally to surgical instruments and more specifically to a fluid supply and suction apparatus for use in endoscopic surgery, laparoscopic surgery, or the like.

BACKGROUND OF THE INVENTION

Surgical tools having both fluid supply and suction capabilities are known to the art. These tools are used in endoscopic and laparoscopic surgery, for hydrodissection, for distension and gynecological procedures, and many other surgical procedures. Endoscopic surgery is a rapidly growing field because it is a less invasive form of surgery.

In general, endoscopic surgery involves a small incision through which one or more hollow tubes are inserted. These hollow tubes are commonly referred to as cannulas and the cannulas can be used to insert a variety of items into the surgical site. Typically, the first item inserted through the cannula is a fiber optic lens which is connected to a video camera on the exterior of the patient. The video camera is attached to a monitor which displays the surgical site so the surgeon need not create a large incision to view his work. Typically, a second cannula is used for the insertion of tools e.g. probes, scissors, cauterization electrodes and the like. Often time a third cannula is necessary to supply sterile saline solution to irrigate the surgical site. A suction line is typically added to allow the saline solution, blood and small pieces of human tissue to be evacuated from the site. Although tools have been created to supply fluid and fluid suction to the surgical site along with a port for the insertion of tools, there has been a continuing need for superior devices which are small, light weight, easy to use and are ergonomically friendly to the surgical personnel.

For instance, a common tool used in endoscopic surgery is a cauterization tool. Cauterization is a process of burning human tissue either to remove a portion of tissue or to cut through the tissue. Typical cauterization tools use electrodes which consist of a thin wire, or set of wires, inserted through the cannula into the surgical site and when a charge is placed across the wires the tissue is burned. However, as is frequently the case cauterization causes the generation of a noxious gas, or smoke which is the natural byproduct of the burning flesh. Often the flesh being burned is diseased and thus the plume of noxious gas is believed to contain pathogens and other potentially harmful airborne byproducts.

Often, the suction line used for fluid was used to evacuate the plume of gas created by cauterization. This presented two problems: 1) the amount of suction required to pull fluid from a surgical site is significantly greater than the suction required to pull gas, thus, often there was too much suction when trying to evacuate the gas causing damage to surrounding tissue; 2) often the gas was evacuated through a line which collected the liquid/gas mixture in a canister meant for liquid fluids only. When the fluid canister was removed from the line to be properly disposed of, the noxious gas, having been collected in the top of the canister, was released to the atmosphere exposing all surgical personnel to the potentially harmful fumes collected in the liquid canister. There has been a need for a dedicated gas evacuation line which can be accurately and finely regulated to provide only enough suction to remove the gaseous plume without disturbing surrounding tissue.

Prior fluid supply and suction apparatuses were generally ergonomically unfriendly. For instance, many have fluid lines entering from one side with the control valves on top requiring the right hand to operate them. This is obviously a problem for "left handed" surgeons or surgical personnel. To complicate matters even further, cannulas are used in both the substantially horizontal and substantially vertical configuration during surgery. The use of a pistol-grip style handle for the fluid supply and suction apparatus solves the problem of allowing either a right handed or left handed surgeon to operate the instrument in the horizontal position. However, when the instrument is placed in a vertical position the pistol-grip becomes very unwieldy and requires the wrist be held in an unnatural position to operate the fluid supply and suction apparatus.

Currently available instruments in the endoscopic field for the supply and evacuation of fluid in a surgical site are relatively complicated and expensive. Rising health care costs have put a premium on the need for inexpensive, relatively simple and reusable devices. Many devices currently on the market are disposable, which saves on the cost of cleaning and sterilizing of the instrument between uses. However, the complexity of the multiple functions performed by a fluid supply and suction apparatus makes disposal after one use a very inefficient cost proposition.

Likewise, the complexity of non-disposable fluid supply and suction apparatuses has caused them to be difficult to clean and reuse. For instance, biasing members, or springs, used in virtually all fluid supply and evacuation apparatuses to control the valves, are notorious for entrapping bits and pieces of tissue, blood and other bio-hazardous material. Likewise, in many devices the valves are not removable or are difficult to remove. Thus, cleaning and sterilization is a very difficult and risky affair. Thus, there has been a need for a simpler, more ergonomically friendly fluid supply and suction device, which segregates and regulates gaseous suction from liquid suction, and is easily dissembled with easily cleaned and sterilized parts.

SUMMARY OF THE INVENTION

It is the primary objective of the present invention to provide an improved fluid supply and suction apparatus for use in a surgical environment.

It is a further objective of this invention to provide a method of introducing fluid and suctioning fluid from a surgical site through a cannula which may or may not contain a surgical tool.

It is also an object of the present invention to provide a fluid supply and suction apparatus which can segregate the removal of gaseous byproducts through a regulated port wherein the suction regulator is capable of fine tune adjustments.

It is yet another object of the present invention to allow the fluid supply and suction apparatus to be operated by either the left hand or the right hand and a horizontal or a vertical configuration with substantially no decrease in comfort when moving from one position to the next.

Another object of the present invention is to provide a substantially unobstructed fluid communication between the fluid suction port and the tool insertion thru-hole.

It is a further object of the present invention that the fluid supply and suction apparatus be relatively simple in construction and either disposable or easily dissembled for cleaning, sterilizing and re-using.

In accordance with one aspect of the present invention there is provided an ergonomic fluid supply and suction apparatus for use in a surgical environment which comprises a body, having a first and second end, a plurality of ports which are in fluid communication with a tool insertion thru-hole. The plurality of ports are open to the first end of the body and the tool insertion thru-hole provides a substantially unobstructed portal from the first end to the second end of the body. There is further provided a plurality of valves which each have a reciprocation control button located on the exterior of the body. Each valve communicates with one of the plurality of ports to control fluid communication between the ports and the tool insertion thru-hole. At least one port is regulated by a suction regulator to selectively control the amount of suction through the regulated port. The fluid supplied and excavated with the suction apparatus are typically gases, liquids and liquids with entrained solid matter or any mixtures thereof. The entrained solid matter will generally be bits and pieces of tissue from the surgical site.

In a preferred embodiment of the present invention there is at least a fluid supply port and a fluid suction port which are in addition to, and separate from, the regulated port. A cannula can be attached to the second end of the body which is opposite the fluid supply port, fluid suction port and the regulated port. The cannula must be in fluid communication with the tool insertion thru-hole. A finger loop and a finger rest are supplied on the body of the fluid supply and suction apparatus which allow the operator to easily hold the fluid supply and suction apparatus in its horizontal and vertical positions respectively. Tubes are generally attached to the fluid supply port and the fluid suction port as well as to the regulated port, and thus, adapters are generally provided for connecting the tubes to the body of the fluid supply and suction apparatus.

In an even more preferred embodiment biasing members are provided for each valve reciprocation control button. The biasing members are below the reciprocation control button and are on the exterior of the fluid supply and suction apparatus body. The valves are also removable. Because the biasing members are substantially segregated from fluid flow within the body of the fluid supply and suction apparatus, the biasing members remain relatively clean and easy to sterilize for re-use. In yet another preferred embodiment of the present invention, the value piston is recessed so that fluid communication between the ports and the tool insertion thru-hole is substantially unrestricted. Further, to provide the least amount of obstruction for the suction port, while maintaining a thin and light weight body, the suction port valve recess is placed at an angle so that the valve piston recess leading edge does not obstruct the suction port.

BRIEF DESCRIPTION OF THE DRAWINGS

While the specification concludes with claims particularly pointing out and distinctively claiming the present invention it is believed that the same will be better understood from the following description taken in conjunction with the accompanying drawings in which:

DETAILED DESCRIPTION OF THE INVENTION

Figure 1:
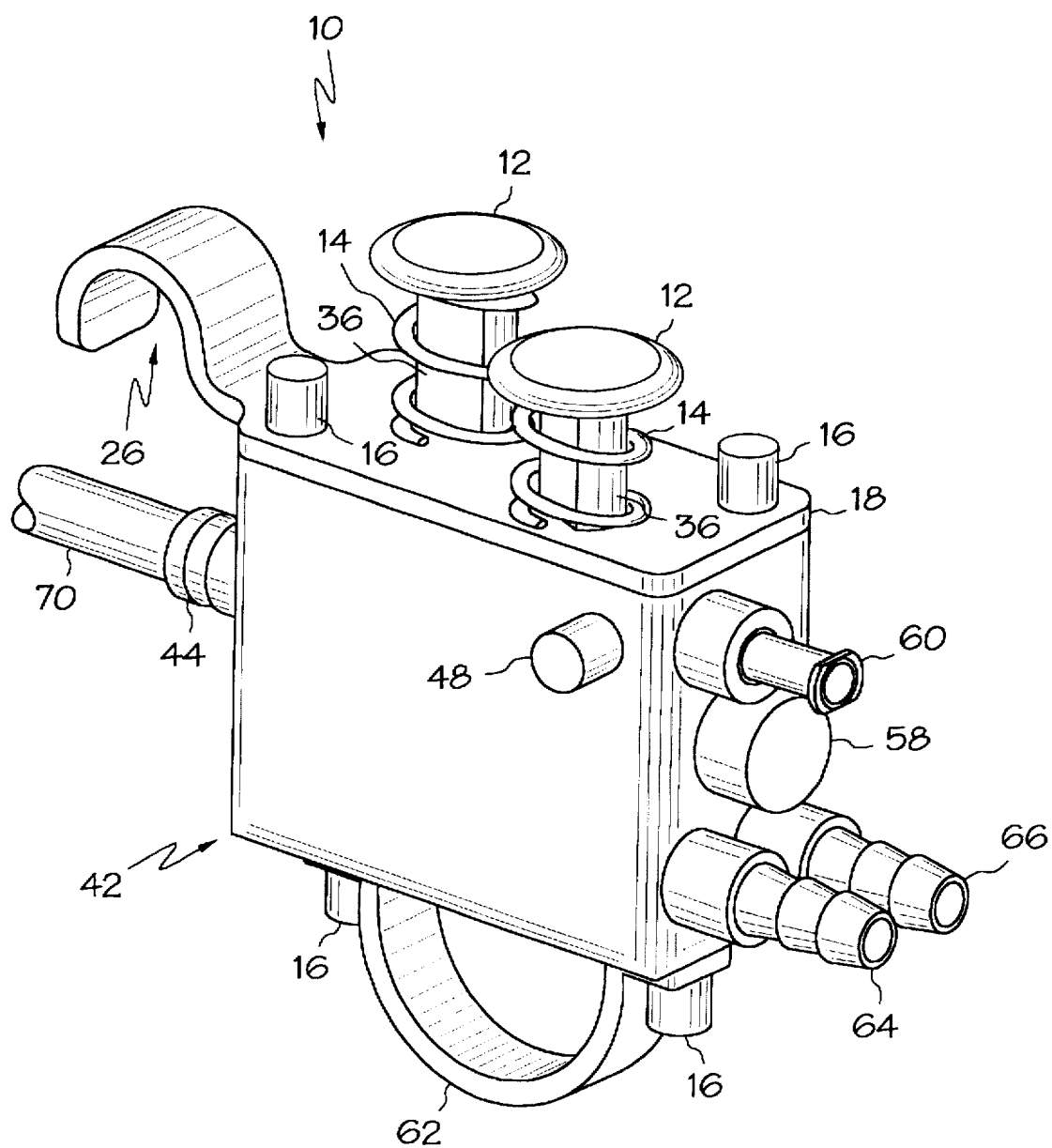
FIG. 1 is an isometric view of a fluid supply and suction apparatus made in conjunction with one aspect of the present invention.

Referring now to the drawings in detail wherein like numerals indicate the same elements throughout the views and where elements having the same final two digits (e.g. 12, 112, 212) indicate comparable elements of various preferred embodiments. FIG. 1 illustrates an exemplary fluid supply and suction apparatus 10.

In one embodiment of the fluid supply and suction apparatus of FIG. 1, there is provided a body 42, a top plate 18 which is connected to body 42 by connectors 16. Top plate 18 is preferably provided with an ergonomic figure rest 26, although finger rest 26 can easily be provided as part of body 42. Attached near the bottom of body 42 is an ergonomic finger loop 62. Finger loop 62 can be manufactured as an integral portion of body 42 or, for ease of manufacture and for ease of cleaning, finger loop 62 can be manufactured separately and connected to body 42 with connectors 16. Although finger rest 26 is shown as being connected to top plate 18 at one end, while finger loop 62 is connected to body 42 at both ends, it will be understood that finger rest 26 could be attached to body 42 at either or both ends and finger loop 62 could likewise be attached to body 42 at one or both ends.

Figure 2:
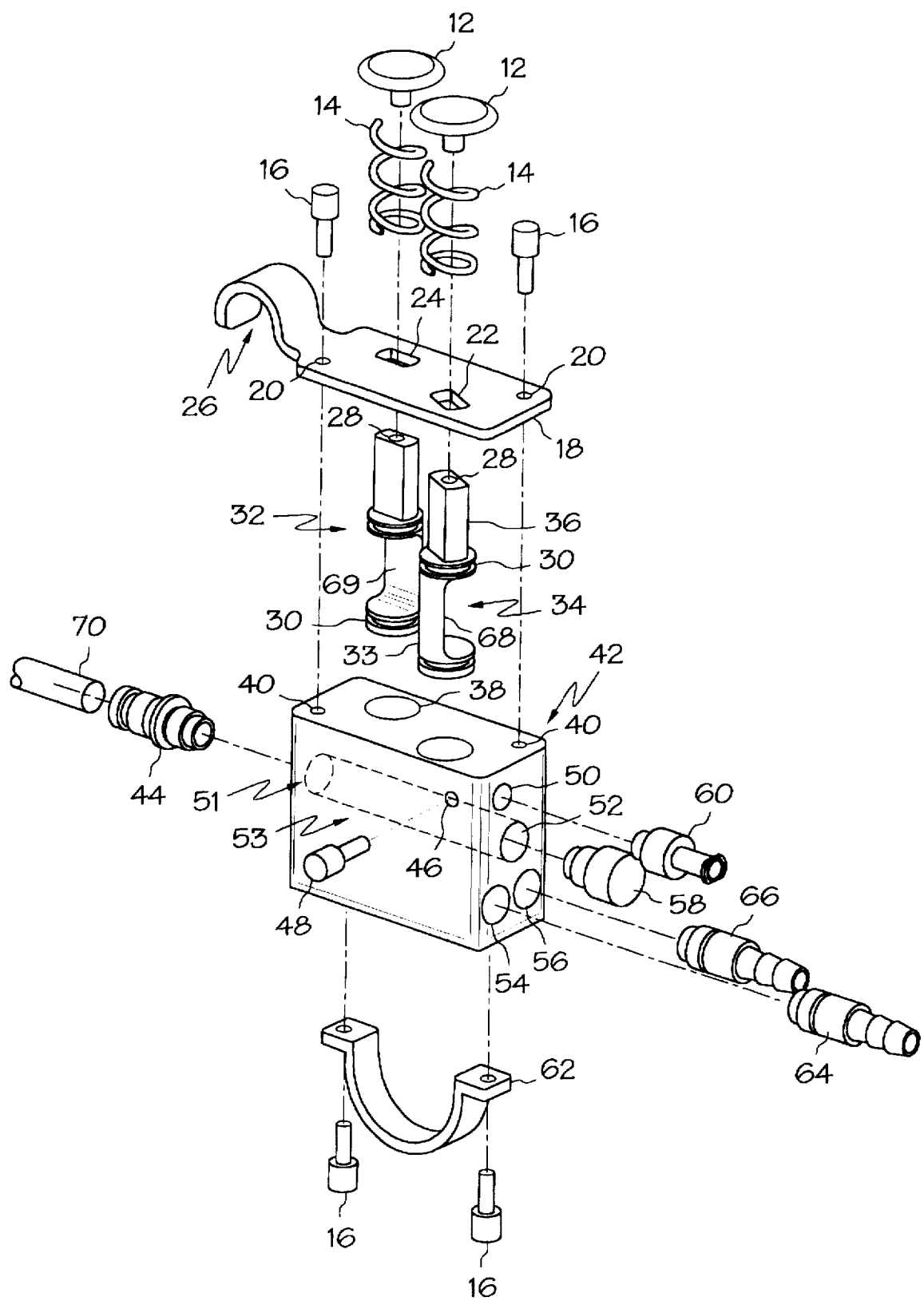
FIG. 2 is an exploded view of the apparatus of FIG. 1.

Protruding from top plate 18 are two valve reciprocation control buttons 12 which are urged into their extended position by biasing members 14 which are preferably placed between the valve reciprocation control button 12 and top plate 18. In the preferred embodiment shown, biasing members 14 are springs and they are wrapped around the valve stems 36. On one side of body 42 is a suction regulator 48. Suction regulator 48 regulates the flow of suction through regulated port 50 as shown in FIG. 2. Regulated port 50 is shown in FIG. 1 with a regulated port adapter 60. Regulated port 50 and regulated port adapter 60 are shown on one end fluid supply and suction apparatus 10. On that same end are the suction port 54 and the fluid inlet port 56 as shown in FIG. 2.

In a preferred embodiment shown, the fluid supply and suction apparatus 10 is further provided with adapters 64 and 66 for the suction port 54 and fluid inlet port 56. On the end of body 42 where the ports are located is the tool insertion thru-hole opening 52, which opens into tool insertion thru-hole 53. In the embodiment shown in FIGS. 1 and 2, thru-hole opening 52 is covered with the tool insertion thru-hole cap 58. At the opposing end of body 42 is a cannula attachment port 51 which is provided with a cannula adapter 44.

As will be appreciated, adapters 60, 66, and 64 can be any appropriate adapter which can receive a fluid supply or suction line, i.e. a hose barb, loure fitting, or the like. Typically, fluid line adapters have exterior threads on one end, thus, interior threads on ports 50, 54, and 56 are typically sufficient to adapt body 42 to a variety of fluid line adapters. However, through standard machining, welding and other metal or plastic working processes, body 42, and more particularly ports 50, 54 and 56, can be adapted to receive virtually any commercially available adapter.

Likewise, tool insertion thru-hole 53 can be adapted at either of its two openings 52 and 51 to receive a variety of caps (e.g. 58), cannula adapters (e.g. 44), fluid line adapters, and the like. During normal endoscopic or laproscopic surgical procedures, a cannula 70 is attached to cannula adapter 44. A cannula is a hollow device which is inserted into an incision giving access to the surgical site. Tools, electrical lines, fluid lines, and the like can be inserted into thru-hole opening 52, passing through tool insertion thru-hole 53, through the hollow catmula adapter 44, and into the hollow cannula 70 to the surgical site. Scalpels, probes, cauterization electrodes and the like can all be inserted through the tool insertion thru-hole 53, through cannula adapter 44 and cannula 70 to the surgical site.

As will be appreciated, when a tool is not being used, tool insertion port cap 58 is preferred to maintain the suction within tool insertion thru-hole 53. Suction is provided through adapter 64 which is connected to suction port 54, where suction port 54 is in fluid communication with tool insertion thru-hole 53. Likewise, fluid is provided through adapter 66, which is attached to fluid supply port 56 which is in fluid communication with tool insertion thru-hole 53.

As is best illustrated in FIG. 2 of a preferred embodiment of the present invention, two valves 32 are provided. Each valve has a valve stem 36, a valve piston 33, a valve piston recess area 34, a valve piston recess leading edge 68, and a valve piston recess face 69. Valves 32 are further provided with a control button connector port 28 which allows the reciprocation control buttons 12 to be easily removed so that top plate 18 can be lifted off and the entire assembly cleaned and sterilized easily. As can be understood, providing valves 32 with removable reciprocation control buttons 12 is a matter of operational convenience and is not necessary for the operation of the fluid supply and suction apparatus 10.

Top plate 18 is further provided with two connector receivers 20 which receive connectors 16 which are secured into apparatus body connector ports 40. Provided in top plate 18 is an angled valve stem port 22 and a valve stem port 24. In a preferred embodiment as shown in FIG. 2, valve piston recess face 69 and valve stem 36 are essentially parallel to one another. Thus, angling valve stem 36 also angles the valve piston recess face with respect to the directional flow into or out of the port which it controls. As is discussed in greater detail below, angled valve stem port 22 allows valve recess area leading edge 68 to be completely removed from suction port 54 as is more clearly shown in FIG. 3.

Valves 32 each communicate with a valve port 38 and a plurality of O-ring grooves 30 are shown. O-rings (not shown) are generally provided to restrict flow from leaving the valve ports 38 or being sucked into valve ports 38 from the exterior of body 42.

Figure 4A:
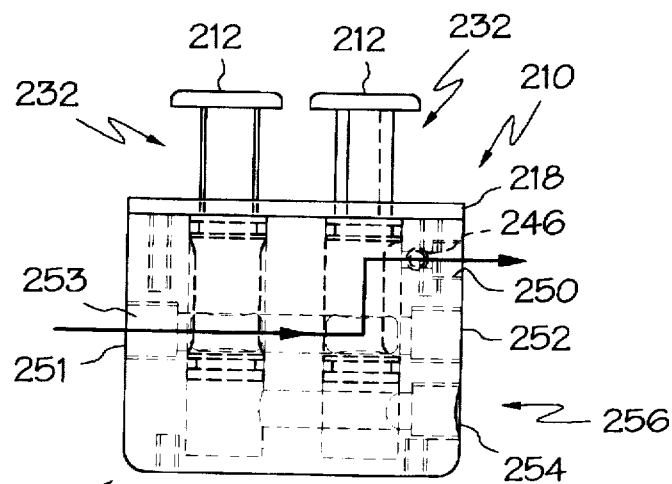
FIG. 4A is a plan schematic of a fluid supply and suction apparatus made in accordance with the present invention showing the proximate flow of fluid material from the surgical site through the tool insertion thru-hole and out the regulated port.
Figure 4B:
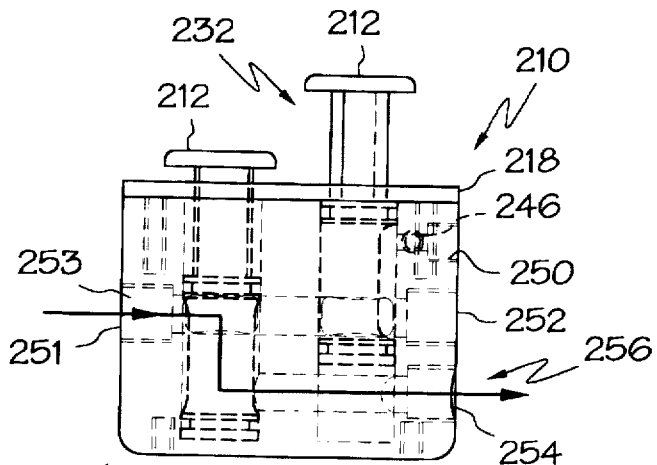
FIG. 4B is a plan schematic of a fluid supply and suction apparatus made in accordance with the present invention showing the proximate flow of fluid material from the surgical site through the tool insertion thru-hole and out the fluid suction port.
Figure 4C:
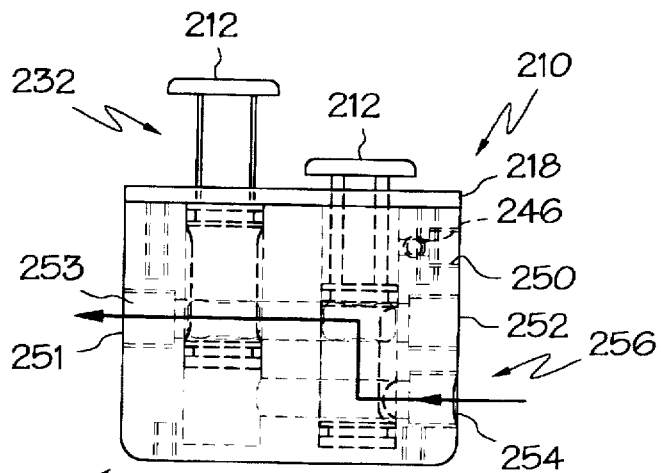
FIG. 4C is a plan schematic of a fluid supply and suction apparatus made in accordance with the present invention showing the proximate flow of fluid material to the surgical site through the tool insertion thru-hole from the fluid supply port.

FIGS. 4A, 4B, and 4C are schematic representations of fluid flow within body 42 of an exemplary fluid supply and suction apparatus 210. In FIG. 4A, both valves 232 are shown in the closed position with the valve reciprocation control knobs 212 in the extended position. As was shown in FIG. 1 and FIG. 2, biasing members 14 would normally hold the reciprocation control knobs in their extended position, however, biasing members have been omitted for purposes of clarity. Ports 254 and 256 are the fluid suction port and fluid supply port respectively. The tool insertion thru-hole 253 is shown with thru-hole opening 252 and cannula attachment port 251. The suction regulated port 250 is also shown, as is suction regulator receptacle 246. The suction regulator receptacle 46, as shown in a preferred embodiment of FIG. 2, receives the suction regulator 48, where suction regulator 48 selectively controls the amount of suction through suction regulated port 250. As can be seen in FIG. 4A, when both valves are in the extended position, suction is pulled through tool insertion thru-hole 253, through the regulated port 250 and out to a collection vessel (not shown).

FIG. 4B shows the valve 232 closest to the cannula attachment port 251 in the depressed position. This permits the valve piston recess area (e.g. FIG. 2, 34) to open fluid communication between tool insertion thru-hole 253 and suction port 254, thus allowing fluid to be evacuated from the cannula attachment port 251, through the tool insertion thru-hole 253 through the valve piston recess area (e.g. FIG. 2, 34) and out through suction port 254.

Likewise, in FIG. 4C, fluid supply port 256, which in this preferred embodiment, is shown parallel to suction port 254, permits fluid to enter the tool insertion thru-hole 253, when the valve closest to the fluid supply port 256 has been depressed. Fluid then travels through the tool insertion through hole 253 out the cannula attachment port 251. The arrangement of valves, and whether suction or supply lines are attached to a particular port are design considerations which can be varied without changing the function of the fluid supply and suction apparatus.

As should be apparent, the discussion of fluid supply and suction with respect to particular valves is an arbitrary distinction and a suction line could easily be attached to a fluid supplied port while the fluid supply port could be attached to the suction port adapter. However, the regulated suction port 250, which is in fluid communication with tool insertion thru-hole 253 while both valves are in their extended position, is preferably limited to the removal of gaseous products. However, regulated fluid supply and the regulated suction of fluid can also be accomplished through the regulated port 250.

As can be understood from FIGS. 4A, 4B, and 4C, during operation of the fluid supply and suction apparatus 210, the tool insertion opening 252 should be closed, e.g. with cap 58, as shown in FIGS. 1 and 2, if a tool is not inserted therethrough. Closing tool insertion opening 252 is necessary to maintain suction and to ensure that fluid flow introduced from fluid supply port 256 leaves the apparatus body 42 from the cannula attachment port 251 and not out of the tool insertion opening 252.

As stated above, fluid supply and fluid suction through the tool insertion through hole 253 is theoretically the same, however, in actual operation the fluid being supplied to a surgical site is a clean, sterile, relatively non-viscous solution, e.g., a saline or glucose solution. However, the material being removed, i.e. the fluid being suctioned, will typically be a mixture of; the fluid which was supplied, i.e. the saline, glucose or other aqueous solution, combined with blood, other body fluids, and bits and pieces of human tissue. It is the presence of the human tissue and other solid matter which has presented significant flow problems for fluid supply and suction apparatuses.

Figure 3:
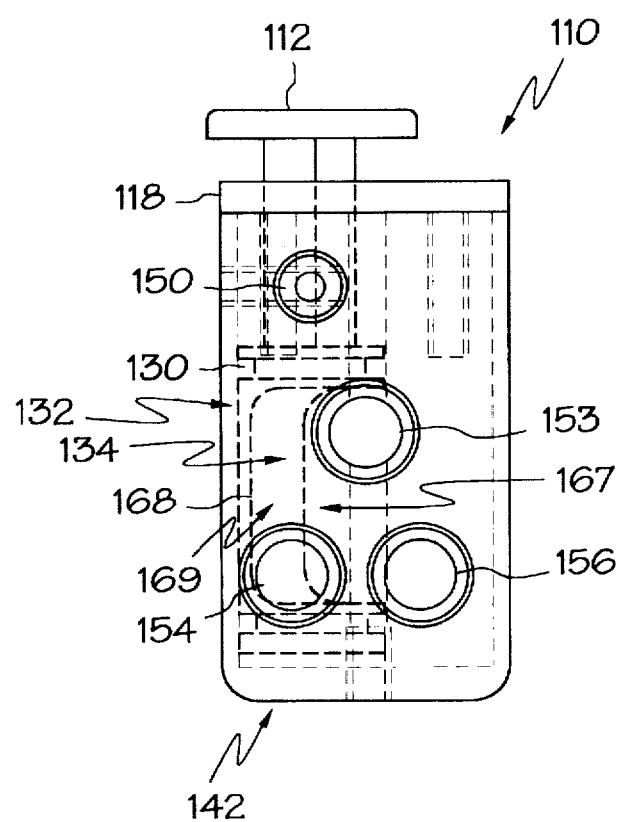
FIG. 3 is a plan schematic, cut-away view showing the inside of a fluid supply and suction apparatus body made in accordance with the present invention, where the suction port valve piston is shown in an angled position in accordance with a preferred aspect of the present invention.

To alleviate the problem of suctioning fluid which contains entrained solid matter such as human flesh, the valve 132, as shown in FIG. 3, which controls fluid from the tool insertion thru-hole 153 to suction port 154, has been placed on an angle. Valve 132 has been angled, as can best be seen in FIG. 2, through the use of angled valve stem port 22. The result of placing valve 132 on an angle is to move valve piston recess face 169 out of the path of suction port 154. Thus, any unnecessary obstruction to the flow of fluid from the tool insertion thru-hole 153 into the valve piston recess area 134 down to the suction port 154 and out into the suction adapter (not shown) and suction line (not shown) has been eliminated. Unobstructed flow is extremely desirable because it reduces the amount of tissue and particulate matter which can be entrained within apparatus body 142 and which might ultimately lead to the restriction of flow out of the surgical site.

Likewise, regulated port 50 and suction regulator 48 are extremely beneficial in the surgical environment because they can be used to provide a reduced suction flow from the surgical site to a dedicated suction line (not shown) which could be attached to regulated port adapter 60. This becomes beneficial when cauterization tools are being employed and tissue within a surgical site is being burned. The burning of tissue in a standard cauterization technique causes the generation of smoke which, not only restricts the view of the surgical site, but can be extremely hazardous because it may contain pathogens and byproducts of the combustion of human flesh.

Removal of this gas is beneficial in that it provides a better view for the surgeon to the surgical site, but more importantly, removal of the smoke through a dedicated line protects the surgical personnel from possible exposure to the pathogens and other byproducts that may be contained in the gas generated by burning. In the past, the gas was evacuated through the normal suction line which presented the problem that the suction could not be effectively regulated and often too much suction was applied. Providing too much suction to the surgical site can move and/or damage tissue being operated on which can ultimately cause damage to the patient. Furthermore, the use of the single suction line collects the gas in a liquid containment vessel which, when removed for disposal, may expose the surgical personnel to escaping gas which is generally an undesirable condition.

As should be apparent, the fluid supply and suction apparatus 10 can be manufactured from a variety of materials. Metals such as stainless steel and titanium can be machined to form the parts necessary to construct the fluid supply and suction apparatus as shown, although other metals are certainly possible. Likewise, most, if not all, of the parts shown can be molded from a variety of commonly available plastics such as Teflon™, high density polypropylene, high density polyethylene, and many others.

Having shown and described the preferred embodiments of the present invention, further adaptation of the fluid supply and suction apparatus and method of introducing fluid into a surgical site and suctioning fluid therefrom described herein can be accomplished by appropriate modifications by one of ordinary skill in the art without departing from the scope of the present invention. A number of alternatives and modifications have been described herein and others will be apparent to those skilled in the art. For example, the positioning of ports and finger rests and finger loops have all been made for the purposes of providing an ergonomic and easy to control instrument for the surgeon or surgical personnel, but other arrangements of ports and finger positioning devices are contemplated. Further examples of alternatives and modifications can be found in the design of the valves, valve bodies, and positioning of the valve bodies to regulate flow within the fluid supply and suction apparatus. Accordingly, the scope of the present invention should be considered in terms of the following claims and is understood not to be limited to the details of the structures and methods shown and described in the specification in the drawings.

I claim:

1. An ergonomic fluid supply and suction apparatus for use in a surgical site comprising:

a body having a first end, a second end, a tool insertion thru-hole providing a substantially unobstructed portal from said first end to said second end of said body, and a plurality of ports in fluid communication with said tool insertion thru-hole, wherein said plurality of ports comprise at least a fluid supply port, a fluid suction port and a suction regulated port;

a plurality of valves, each valve having a reciprocation control button located on the exterior of said body, said valves each communicating with one of said plurality of ports to control the flow of a fluid such as gases, liquids, liquids with entrained solid matter or mixtures thereof between said ports and said tool insertion thru-hole;

said suction regulated port having a suction regulator to selectively control the amount of suction through said suction regulated port.

2. The fluid supply and suction apparatus of claim 1, wherein fluid is supplied or removed from said surgical site through a cannula attached to said second end of said body, said cannula being in fluid communication with said tool insertion thru-hole.

3. The fluid supply and suction apparatus of claim 1, wherein said body further comprises a finger loop and a finger rest attached thereto.

4. The fluid supply and suction apparatus of claim 1, wherein said fluid supply port, said fluid suction port, and said suction regulated port can each be individually adapted to receive a fluid tube.

5. The fluid supply and suction apparatus of claim 1, wherein each of said plurality of valves includes a biasing member located between said body and said reciprocation control button, said biasing members being substantially segregated from fluid flow within said body.

6. The fluid supply and suction apparatus of claim 1, wherein said plurality of valves are removable.

7. The fluid supply and suction apparatus of claim 1, wherein fluid flow through said fluid suction port is controlled by one of said valves, having a valve piston that is normally in a position that prevents substantially all fluid flow through said fluid suction port, and when said valve reciprocation control button is depressed, said fluid suction port is substantially unobstructed by said valve piston.

8. The fluid supply and suction apparatus of claim 1, wherein said suction regulated, is for gas evacuation port.

9. A method for introducing or removing fluids from a surgical site comprising the steps of:

providing an ergonomic fluid supply and suction apparatus comprising;

a body having a first end, a second end, a tool insertion thru-hole providing a substantially unobstructed portal from said first end to said second end of said body, and a plurality of ports in fluid communication with said tool insertion thru-hole, wherein said plurality of ports comprise at least a fluid supply port, a fluid suction port, and a suction regulated port, and a cannula attached to said second end of said body, said cannula being in fluid communication with said tool insertion thru-hole;

further providing;

a plurality of valves each having a reciprocation control button located on the exterior of said body, said valves each communicating with one of said ports to control the flow of a fluid between said port and said tool insertion thru-hole, said suction regulated port having a suction regulator to selectively control the amount of suction through said suction regulated port;

supplying or removing fluid to or from said surgical site through said cannula and said tool insertion thru-hole;

controlling fluid flow through said tool insertion thru-hole by selective operation of said valves and said suction regulator; and wherein said fluid comprises gasses, liquids, liquids with entrained solid matter or mixtures thereof.

10. The method of claim 9, wherein said fluid supply port, said fluid suction port, and said suction regulated port can each be individually adapted to receive a fluid tube.

11. The method of claim 9, wherein each of said plurality of valves includes a biasing member located between said body and said reciprocation control button, said biasing members being substantially segregated from fluid flow within said body.

12. The method of claim 9, wherein said plurality of valves are removable.

13. The method of claim 9, wherein fluid flow through said fluid suction port is controlled by one of said valves, having a valve piston that is normally in a position that prevents substantially all fluid flow through said fluid suction port, and when said valve reciprocation control button is depressed said fluid suction port is substantially unobstructed by said valve piston.

14. The method of claim 9, wherein said suction regulated is for gas evacuation port.

* * * * *

UNITED STATES PATENT AND TRADEMARK OFFICE
CERTIFICATE OF CORRECTION

PATENT NO. : 5,722,949
DATED : March 3, 1998
INVENTOR(S) : Christopher N. Sanese It is certified that error appears in the above-indentified patent and that said Letters Patent is hereby corrected as shown below:

In claim 8, line 2, delete ","; insert the word --port-- after the word "regulated"; and delete the word "port" , after "evacuation".

In claim 14, line 1, insert the word --port-- after the word "regulated"; and in line 2, delete the word "port".

Signed and Sealed this

Twenty-third Day of June, 1998

Attest:

BRUCE LEHMAN

*Attesting Officer*    *Commissioner of Patents and Trademarks*